United States Patent
Kollmer

(10) Patent No.: US 9,247,963 B2
(45) Date of Patent: Feb. 2, 2016

(54) BONE COMPRESSION DEVICE AND METHODS

(75) Inventor: Charles Kollmer, Edgewater, FL (US)

(73) Assignee: Charles Kollmer, Edgewater, FL (US)

( * ) Notice: Subject to any disclaimer, the term of this patent is extended or adjusted under 35 U.S.C. 154(b) by 445 days.

(21) Appl. No.: 13/057,824

(22) PCT Filed: Jul. 30, 2009

(86) PCT No.: PCT/US2009/052182
§ 371 (c)(1),
(2), (4) Date: Feb. 7, 2011

(87) PCT Pub. No.: WO2010/019384
PCT Pub. Date: Feb. 18, 2010

(65) Prior Publication Data
US 2011/0137356 A1  Jun. 9, 2011

Related U.S. Application Data

(60) Provisional application No. 61/088,040, filed on Aug. 12, 2008.

(51) Int. Cl.
*A61B 17/88* (2006.01)
*A61B 17/68* (2006.01)
(Continued)

(52) U.S. Cl.
CPC ........... *A61B 17/683* (2013.01); *A61B 17/1767* (2013.01); *A61B 17/842* (2013.01); *A61B 17/864* (2013.01); *A61B 17/8665* (2013.01); *A61B 17/8695* (2013.01); *A61B 17/8866* (2013.01)

(58) Field of Classification Search
CPC ................. A61B 17/683; A61B 17/68; A61B 2017/681; A61B 17/1767; A61B 17/842; A61B 17/864; A61B 17/8665
USPC .......... 606/300–309, 322–324, 329; 623/20.18–20.2, 20.18–20.2; 411/338, 411/5, 40, 42, 55
See application file for complete search history.

(56) References Cited

U.S. PATENT DOCUMENTS 2,485,531 A  1/1948  Dzus et al.
2,489,870 A * 11/1949  Dzus .............................. 606/310
(Continued)

FOREIGN PATENT DOCUMENTS

DE  202007017159 U1  5/2008
EP  0 792 621  * 3/1997 ............. A61B 17/04

OTHER PUBLICATIONS

"PCT International Search Report dated Oct. 29, 2009 for PCT/US2009/052182, from which the instant application is based," 4 pgs.
(Continued)

*Primary Examiner* — Anu Ramana
*Assistant Examiner* — Jessica Weiss
(74) *Attorney, Agent, or Firm* — Mark Malek; William Harding; Widerman Malek, PL

(57) ABSTRACT

Embodiments of the invention provide a bone compression device for fixing first and second bone fragments together. The device includes an elongated fastener threadedly receivable within an anchor and a lock movably positioned within the anchor bore to lock the fastener and anchor against relative rotation. The lock may include an externally threaded locking screw threadedly receivable within the anchor coaxial with the fastener shank. The locking screw can be advanced within the anchor bore to lock the position of the fastener shank portion within the anchor bore. Embodiments of the device may be inserted within first and second bores formed in two bone fragments and tightened to compress the two bone fragments together.

19 Claims, 15 Drawing Sheets

(51) Int. Cl.
*A61B 17/17* (2006.01)
*A61B 17/84* (2006.01)
*A61B 17/86* (2006.01)

(56) References Cited

U.S. PATENT DOCUMENTS

| | | | |
|---|---|---|---|
| 2,511,051 A * | 6/1950 | Dzus | 81/451 |
| 3,917,299 A * | 11/1975 | Anderson | 280/607 |
| 5,203,770 A * | 4/1993 | Wigness et al. | 604/506 |
| 5,827,285 A | 10/1998 | Bramlet | |
| 5,849,004 A | 12/1998 | Bramlet | |
| 5,976,139 A | 11/1999 | Bramlet | |
| 5,984,970 A | 11/1999 | Bramlet | |
| 6,183,474 B1 | 2/2001 | Bramlet et al. | |
| 6,302,887 B1 * | 10/2001 | Spranza et al. | 606/916 |
| 6,355,043 B1 | 3/2002 | Adam | |
| 6,443,954 B1 | 9/2002 | Bramlet et al. | |
| 6,447,546 B1 | 9/2002 | Bramlet et al. | |
| 6,488,684 B2 | 12/2002 | Sterghos et al. | |
| 6,632,224 B2 | 10/2003 | Cachia et al. | |
| 6,648,889 B2 | 11/2003 | Bramlet et al. | |
| 6,695,844 B2 * | 2/2004 | Bramlet et al. | 606/66 |
| 8,585,744 B2 * | 11/2013 | Duggal et al. | 606/301 |
| 2002/0198527 A1 * | 12/2002 | Muckter | 606/73 |
| 2005/0165492 A1 * | 7/2005 | Fitz | 623/20.19 |
| 2006/0149235 A1 * | 7/2006 | Jackson | 606/61 |
| 2006/0264944 A1 * | 11/2006 | Cole | 606/62 |
| 2007/0225716 A1 * | 9/2007 | Deffenbaugh et al. | 606/69 |
| 2007/0225819 A1 * | 9/2007 | Eva | 623/20.14 |
| 2009/0326533 A1 * | 12/2009 | Dell'Oca | 606/64 |

OTHER PUBLICATIONS

"PCT Written Opinion dated Oct. 29, 2009 for PCT/US2009/052182, from which the instant application is based," 7 pgs.

* cited by examiner

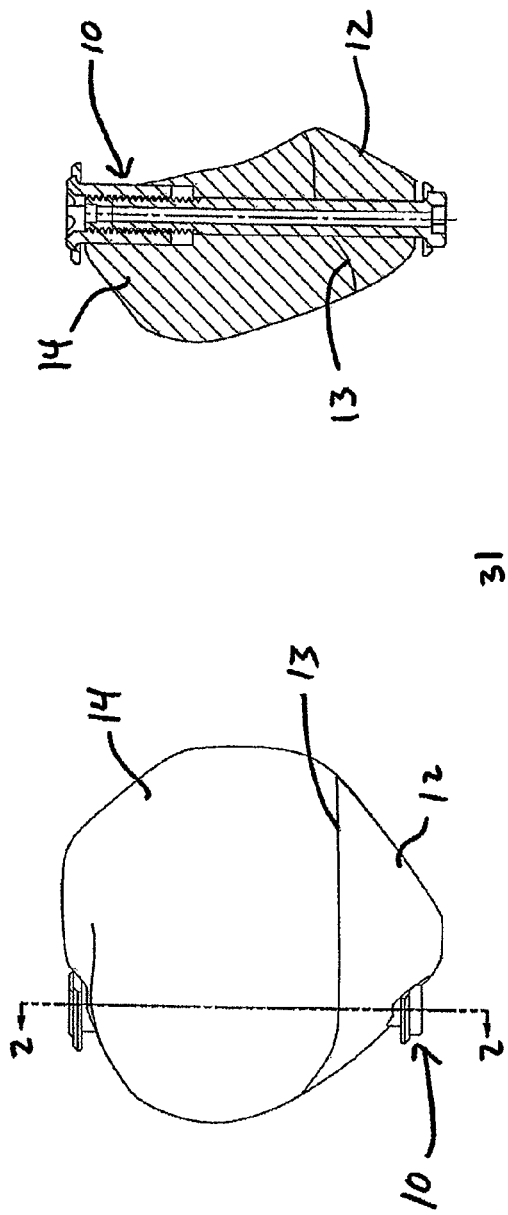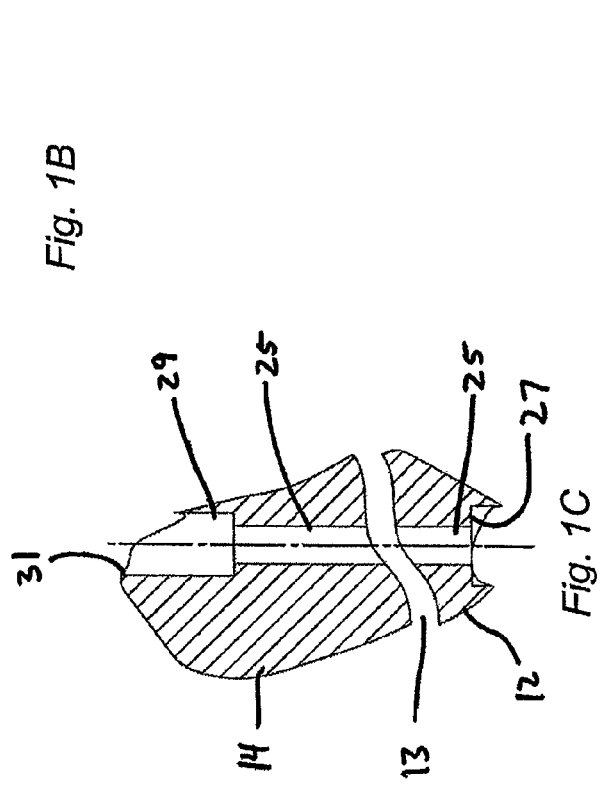

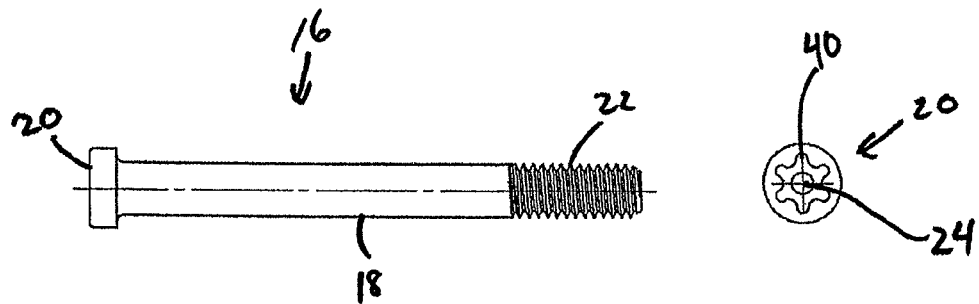
Fig. 4A
Fig. 4B
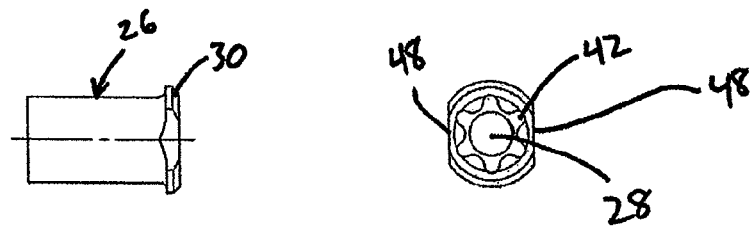
Fig. 5A
Fig. 5B
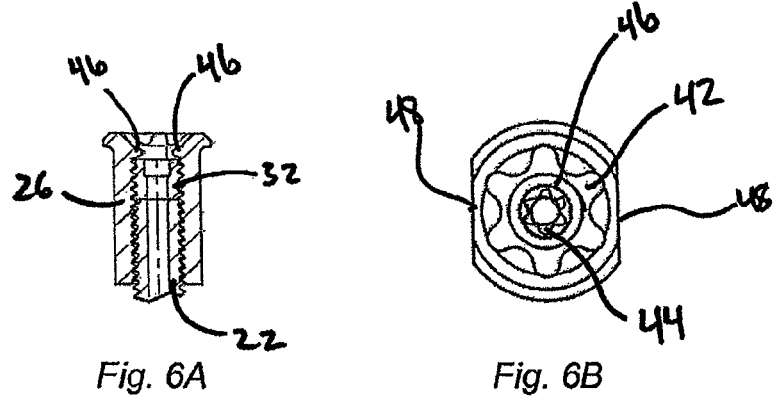
Fig. 6A
Fig. 6B

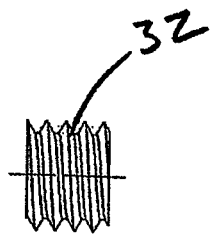
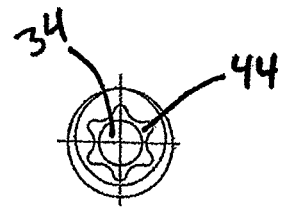
Fig. 7A         Fig. 7B
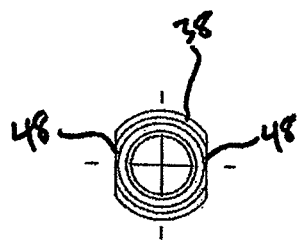
Fig. 8A         Fig. 8B
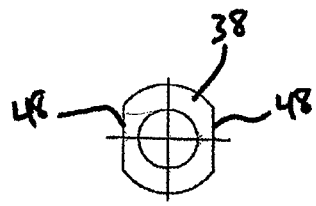
Fig. 8C

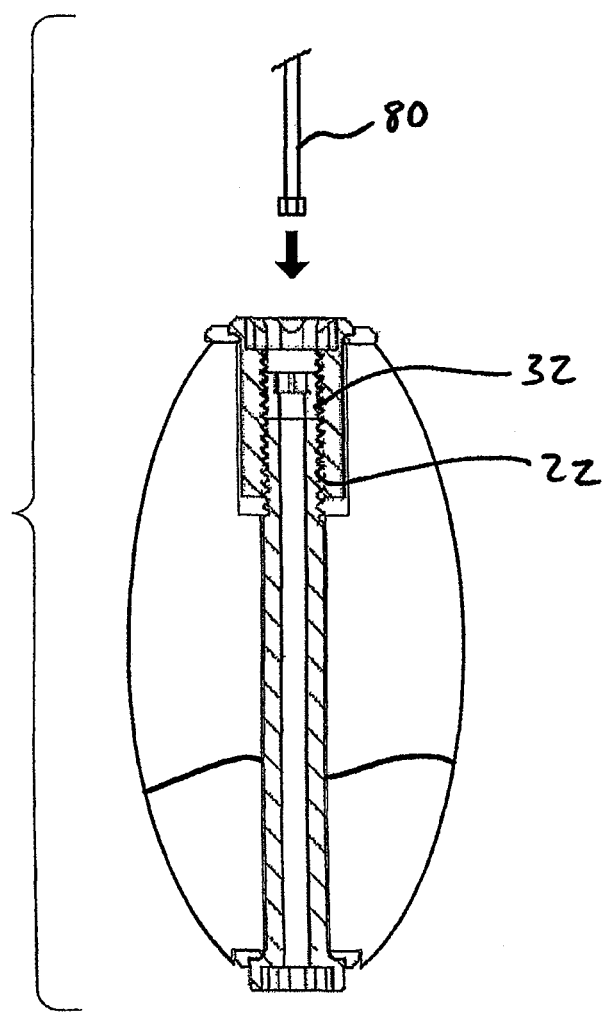

BONE COMPRESSION DEVICE AND METHODS

RELATED APPLICATIONS

This application is a 35 U.S.C. 371 national stage filing from International Application No. PCT/US2009/052182 filed Jul. 30, 2009 and claims priority to U.S. Provisional Patent Application No. 61/088,040, filed Aug. 12, 2008, the teachings both of which are incorporated herein by reference.

FIELD

Embodiments of the invention generally relate to devices and methods for fixing together two or more bone fragment following a fracture. More particularly, some embodiments relate to devices for compressing bone fragments together along fracture surfaces.

BACKGROUND

Fractured bone fragments typically must be held together for extended time periods to promote healing. Adjoining fragments of a severed or fractured bone are typically clamped together or attached to one another through the use of pins or screws driven through the separated portions of bone, or are fixed in place using a splint.

In general, bones are formed of a relatively soft, spongy cancellous material surrounded by a much harder cortex. Cancellous bone yields under relatively low loading, while the much denser cortical bone supports much higher loading. In some cases, fixation devices are used to secure the broken parts together through direct fixation in the bone. However, due to the soft nature of the cancellous material, fixation devices may tend to disassemble as screws and nails loosen from the bone material over time.

In some cases, compression screws are used to compress together bone fragments. Given relatively high loading, compression screws can tend to back out once implanted, thus leading to unwanted discomfort and potentially recurring surgery. While a number of techniques and devices have been developed for fixing bones together for healing, these and other issues remain. Thus, an improved bone compression device with strong purchase and no backing out is desired.

SUMMARY

According to a first aspect of the invention, a bone compression device for compressing together first and second bone fragments is provided. The compression device generally includes an elongated fastener with an externally threaded portion, an anchor with an internally threaded bore for threadedly receiving the externally threaded portion of the fastener and a lock for locking together the fastener and the anchor against relative rotation. The lock may be in the form of an externally threaded locking screw threadedly receivable within the anchor, coaxial with the fastener portion. In an operative position, the locking screw may be advanced within the anchor bore to lock the position of the fastener portion within the anchor bore.

In some embodiments the fastener is insertable through a first bore formed in the first and second bone fragments such that the fastener shank portion extends through the first bone fragment into the second bone fragment. The fastener may include an enlarged head portion engaging a rim of the first bore in the first bone fragment. The anchor is insertable into a second bore formed in the second fragment, the second bore being of greater diameter than the first bore and coaxial with the first bore. An anchor shoulder engages a rim of the second bore such that in an operative position the anchor shoulder and the fastener head portion compress the first and second bone fragments together.

In certain embodiments the bone compression device may include an exterior washer about the fastener and/or anchor for engaging the bore rims and forming part of the fastener head portion and anchor shoulder portions, respectively. In some cases the washers may include opposing flat edges that can be rotatably positioned against the often curved bore rims to limit protrusion of the fastener from the first bore and/or the anchor from the second bore.

Some exemplary anchors include an internally extending lip about the second end of the anchor, which provides access to an externally threaded locking screw while preventing the locking screw from being removed through the second end of the anchor. The lip may extend about substantially the entire circumference of the anchor's internally threaded bore at the second end of the anchor, or may be provided as one or more segments protruding into the bore of the anchor.

Further, in some embodiments, at least one of the fastener head portion, the anchor second end, and the locking screw include a drive portion, such as a configured recess for engaging a twisting or driving tool such as a screwdriver. For example, the drive portion may include a hexalobular configuration. In some cases the anchor drive portion extends about the circumference of the anchor second end while providing access to the locking screw drive portion within the anchor bore.

In some embodiments a bone compression device may include a fastener with a threaded shank portion that is threadingly received within the anchor when the fastener and anchor are operably positioned to compress the first and second bone fragments to a desired degree. In addition, the compression device components may include a biocompatible material, such as, for example, titanium, or another biologically acceptable material.

Further, in some embodiments the second end of the fastener shank and the locking screw are adapted to deform when tightened against each other. This can help lock the position of the fastener shank within the anchor threaded bore. In another example, the device may include a deformable insert that may be positioned within the anchor bore between the second end of the fastener shank and the locking screw. When the fastener shank and the locking screw are tightened against each other, the insert deforms to lock the position of the fastener shank within the anchor. In some cases the deformable insert may include a biologically acceptable polymer.

According to another aspect of the invention, a method of fixing first and second bone fragments using a bone compression device is provided. In addition to providing a bone compression device according to embodiments of the invention, a first bore may be formed through the first bone fragment and at least partially through the second bone fragment, while a second larger bore may be formed through the second bone fragment connecting to and coaxial with the first bore. The method includes inserting the first end of the anchor into the second bore so that the anchor shoulder engages the rim of the second bore, and inserting the fastener through the first and second bores to advance the fastener into the first end of the anchor so that the fastener head portion engages a rim of the first bore and the fastener and anchor compress the first and second bone fragments together. Further, a lock, such as a locking screw, is coaxially advanced through the anchor towards the fastener to engage the second end of the fastener shank portion and to lock together the fastener and the anchor.

Methods of using a bone compression device may further include forming a countersunk depression in the first bone fragment about the rim of the first bore and/or forming a countersunk depression in the second bone about the rim of the second bore to accommodate the fastener head, the anchor shoulder, and/or one or more washers. In some cases the end of the second bore at its interface with the first bore is squared-off and a separation is maintained between the end of the second bore and the first end of the anchor when the anchor shoulder engages the rim of the second bore.

In some embodiments, the method further includes providing one or more washers about the anchor and/or the fastener. The washers may in some cases be rotatable to limit protrusion of the fastener from the first bore and/or the anchor from the second bore. In some cases the locking screw may be inserted into the anchor prior to inserting the anchor into a bore. The locking screw may then be prevented from being removed from the exterior end of the anchor, for example, by a rounded lip protruding inwardly at the exterior end of the anchor.

In some embodiments, a method further includes selecting the fastener of the first bone compression device from a plurality of fasteners of different lengths, such that the threaded portion of the fastener shank will be substantially received within the anchor when the fastener and anchor compress the first and second bone fragments to a desired degree. A Kirschner wire may be passed through the first and second bone fragments as a guide for forming the first and second bores. In some cases, a cannulated clamp may temporarily fix the bone fragments together, the cannulated clamp jaws serving to guide the K wire as it is inserted into the bone.

In general, methods according to embodiments of the invention may be directed to fixing bone fragments forming at least a portion of a patella, a femur, a tibia, a calcaneus, a humerus, or other bone. Procedures using the bone compression device may be completed subcutaneously, or as part of an open surgery. Two or more bone compression devices may be used to secure the bone fragments, and circlage wires may be used to further stabilize the fracture.

According to another aspect of the invention, a kit for compressing together first and second bone fragments may include a plurality of elongated fasteners of different lengths, one or more anchors and locks, and a plurality of driving tools for advancing and securing the fasteners, the anchor, and the locks. The kit may further include a plurality of Kirschner wires, a cannulated clamp, a plurality of tension bands, or a deformable insert.

BRIEF DESCRIPTION OF THE DRAWINGS

FIG. 1A is a front view of two bone fragments fixed by a bone compression device according to an embodiment of the invention;

FIG. 1B is a cross-section view of the bone fragments and bone compression device of FIG. 1A along the section 2-2;

FIG. 1C is a cross-section view of the bone fragments of FIGS. 1A and 1B without the bone compression device;

FIG. 4A is a side view of an elongated fastener according to an embodiment of the invention;

FIG. 4B is an end view of a head of the elongated fastener of FIG. 4A;

FIG. 5A is a side view of an anchor according to an embodiment of the invention;

FIG. 5B is an end view of a drive head of the anchor of FIG. 5A;

FIG. 6A is a partial cross-section view of an assembled anchor, fastener and locking screw;

FIG. 6B is a top view of the assembly of FIG. 6A;

FIG. 7A is a side view of a locking screw according to an embodiment of the invention;

FIG. 7B is an end view of the locking screw of FIG. 7A;

FIG. 8A is a front view of a washer according to an embodiment of the invention;

FIG. 8B is a side view of the washer of FIG. 8A;

FIG. 8C is a back view of the washer of FIG. 8A;

FIG. 16a illustrates seating of the locking screw of FIG. 16; and

DETAILED DESCRIPTION OF THE PREFERRED EMBODIMENTS

Figure 2A:
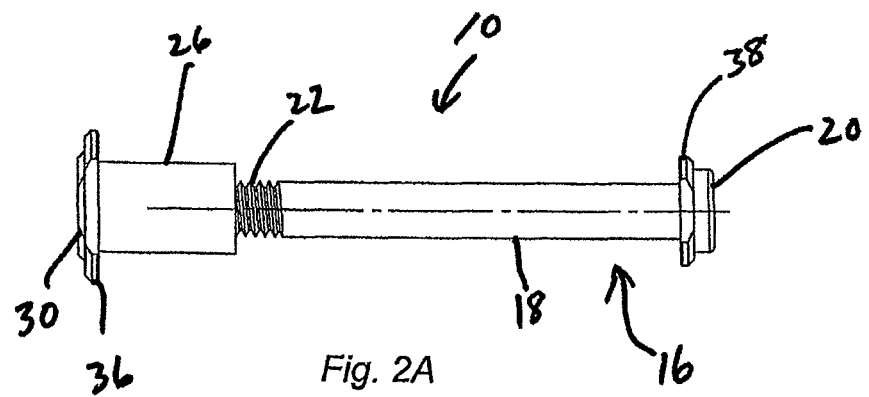
FIG. 2A is a side view of an assembled bone compression device according to an embodiment of the invention.

The following detailed description should be read with reference to the drawings, in which like elements in different drawings are numbered identically. It will be understood that embodiments shown in the drawings and described herein are merely for illustrative purposes and are not intended to limit the invention to any embodiment. On the contrary, it is intended to cover alternatives, modifications, and equivalents as may be included within the scope of the invention as defined by the appended claims.

Embodiments of the present invention provide a bone compression device and methods for compressing bone that are particularly suited for holding together two or more bone fragments, to permit the bone fragments to knit together. According to some embodiments, the bone compression device is particularly suited for fractures of the patella. However, the invention is not restricted to any particular anatomy and may be helpful in fixing a wide variety of bones.

FIGS. 1A and 1B illustrate a bone compression device 10 that is used to fix a first bone fragment 12 and a second bone fragment 14 according to an embodiment of the invention. As shown in FIGS. 1A and 1B, the bone compression device 10 is adapted to compress together the fractured portions of a patella according to this embodiment; that is, to reduce the fracture 13 by compressing the bone fragments together along the fracture line.

Figure 2B:
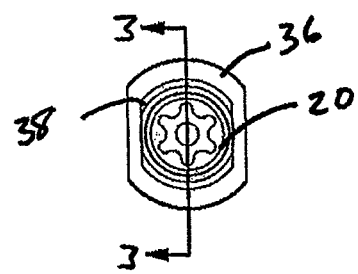
FIG. 2B is an end view of the bone compression device of FIG. 2A taken from the right end of FIG. 2A.
Figure 2C:
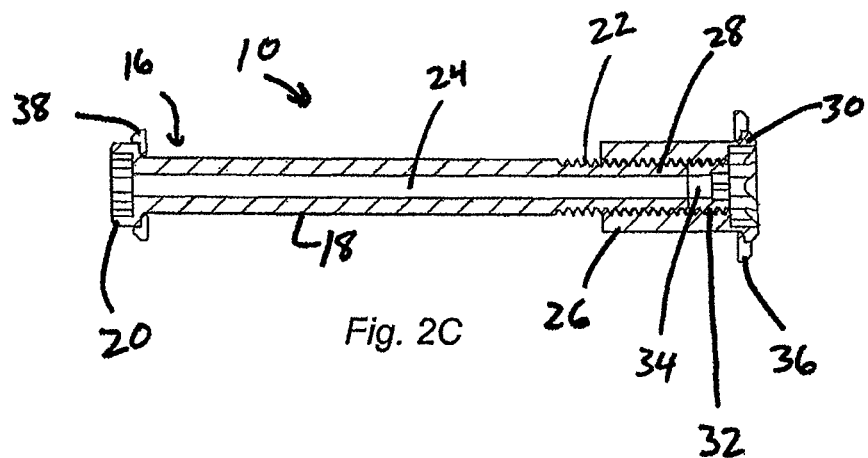
FIG. 2C is a cross-section view of the bone compression device of FIGS. 2A and 2B taken along section 3-3 of FIG. 2B.
Figure 3:
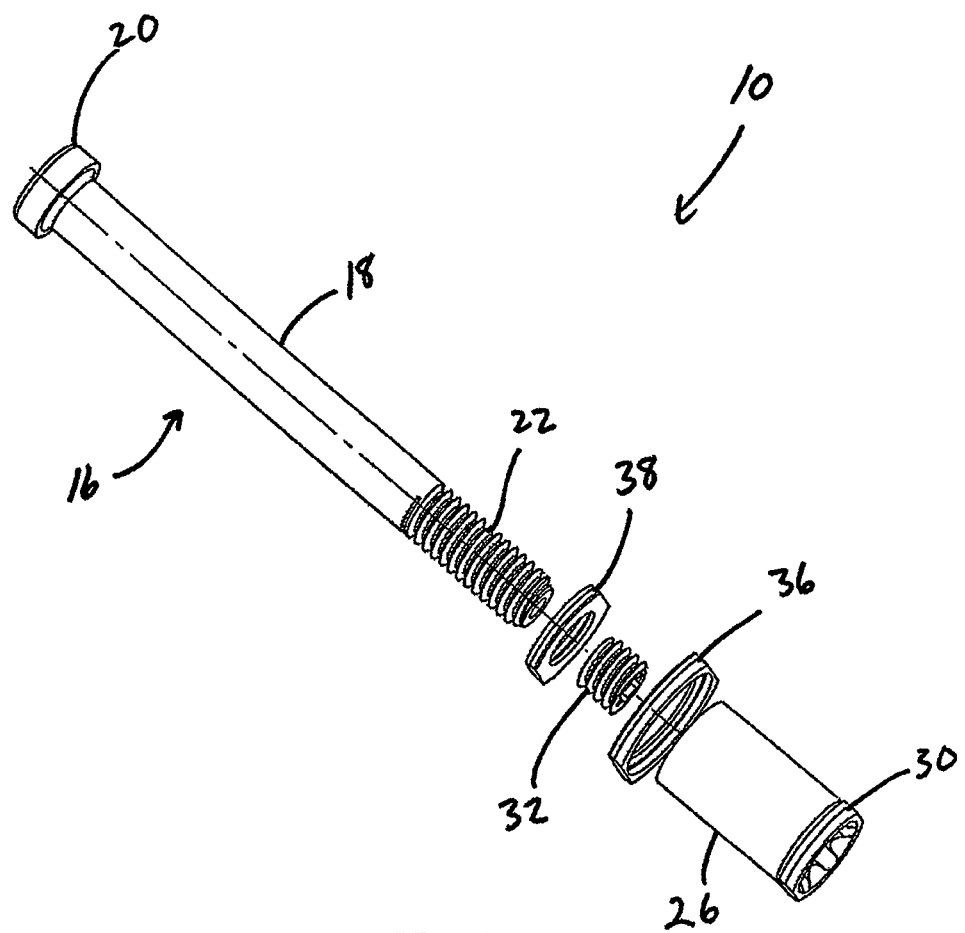
FIG. 3 is an exploded view of the bone compression device of FIG. 2A.

FIGS. 2A-2C illustrate various views of the assembled bone compression device 10, and FIG. 3 illustrates an exploded view of the bone compression device 10. According to certain embodiments, the bone compression device 10 includes an elongated fastener 16 having a shank portion 18 with an enlarged head portion 20 at one end and an externally threaded portion 22 at the other end. A bore 24 extends through the head and shank portions providing access through the fastener 16. As an example, the fastener 16 may comprise an exteriorly threaded, cannulated bolt with an enlarged cap at one end.

As shown, an anchor 26 is provided with an internally threaded bore 28 for threadedly receiving the externally threaded shank portion 22 of the fastener 16. The shank is received in a first end of the anchor, while a second end of the anchor includes an enlarged shoulder 30. As an example, the anchor may comprise an internally threaded compression nut.

Referring briefly to FIGS. 1B and 1C, the fastener 16 and anchor 26 are insertable into the first and second bone fragments, respectively. When assembled and tightened together, the head portion 20 of the fastener 16 and the shoulder 30 of the anchor 26 compress the bone fragments together to close and compress the fracture. For example, with more particular reference to FIG. 1C, the fastener 16 is insertable through a first bore 25 formed in the first and second bone fragments. The shank portion 18 extends through the first bone fragment 12 into the second bone fragment 14. Upon insertion, the head portion 20 of the fastener engages the rim 27 of the first bore 25 to prevent the fastener from further entering the bone fragments. The anchor 26 is insertable into a second larger diameter bore 29 formed in the second bone fragment 14. The anchor shoulder 30 engages a rim 31 of the second bore 29 so that as the fastener 16 and anchor 26 are tightened together, the anchor shoulder 30 and the fastener head portion 20 transmit compressive force to the bone fragments about the respective bore rims to compress the first and second bone fragments together.

According to some embodiments, the second bore 29 is coaxial with the first bore 25, and has a substantially greater diameter than the first bore. In addition, the first and second bores 25, 29 are preferably formed with diameters that are the same or very slightly larger than the threaded portion of the fastener shank 22 and the outside diameter of the anchor 26, respectively. Accordingly, the outside diameter of the anchor is substantially greater than the diameter of the threaded shank portion 22 of the fastener according to some embodiments. Thus, a snug press fit is desirably provided.

In certain embodiments of the invention, the bone compression device 10 serves not only to compress bone fragments together, e.g., reduce a fracture and hold fractured surfaces together for healing, but also, due to the rigid nature of the device, tends to support the reduced fracture against bending stresses encountered by the first and second bone fragments. For example, when placed within a patella, the device 10 may support the patella fragments against forces by the quadriceps and patella tendons that otherwise may cause the fracture to open anteriorly. In such an embodiment, the bending moment particularly could be in the vicinity of the fracture line, and thus the compression device is configured to be quite strong and resistant to bending moments at this location. For example, the length of the threaded shank portion 22 may be short enough to be substantially received within the anchor 26 so as to largely avoid stress concentrations in the threaded area.

In some embodiments, the bone compression device may include one or more washers. Referring to FIGS. 2A-2C and 3, a first washer 36 may be provided about the circumference of the anchor 26, which engages the shoulder 30 and the rim 31 to transmit and spread the compressive force from the anchor shoulder 30 about the rim 31 of the second bore 29. A second washer 38 may be provided about the fastener 16 to likewise engage the head portion 20 of the fastener and the rim 27 of the first bore 25 to transmit and spread the compressive force from the head portion about the rim. In some embodiments, the first and second washers 36, 38 may be formed as part of the anchor shoulder 30 and fastener head portion 20, respectively.

Referring to FIG. 2C and FIG. 3 and also FIGS. 7A and B, according to one embodiment, the bone compression device 10 includes a lock within the anchor bore 28 adapted to lock the fastener 16 and anchor 26 against relative rotation. For example, the lock may include a locking screw or a lock nut. In one embodiment, the lock may be in the form of an externally threaded lock nut having an internally threaded bore. The lock nut is threadedly received within the anchor bore 28. The end of the threaded fastener portion 22 may be slightly smaller in diameter than the anchor bore 28 so as to be received within the bore of the lock nut. The lock nut may then be tightened against the end of fastener to lock the position of the fastener within the anchor.

In one embodiment, the lock may be in the form of an externally threaded locking screw 32 with an internal bore 34. For example, the locking screw 32 may comprise a cannulated, externally threaded bolt section. The locking screw 32 is receivable within the internally threaded bore 28 of the anchor 26 and can be advanced coaxially against the confronting end of the threaded shank portion 22 to lock the position of the shank within the anchor 26. Thus, when the bone compression device 10 is assembled within a body, the locking screw 32 prevents the anchor 26 and the fastener 16 from inadvertently disengaging, e.g., under stress or movement. For ease of understanding, the following description refers to the lock as the locking screw 32.

The bone compression device 10 typically comprises a biocompatible material according to some embodiments. For example, the fastener 16, the anchor 26, and the locking screw 32 may comprise titanium or other biologically acceptable metal. In some embodiments, the threaded shank 22 of the fastener, the thread of the locking screw 32, and/or the internally thread in the anchor bore 28 of the anchor 26 may comprise a material that deforms slightly under exerted pressure. For example, as the fastener 16 and locking screw 32 are tightened against each other, one of the pieces may deform slightly so as to lock the fastener shank within the anchor's threaded bore. In some embodiments, the bone compression device 10 may include a deformable insert (not depicted) placed within the anchor bore between the end of the threaded fastener shank 22 and the locking screw 32. As the pieces are tightened together, the insert deforms, thus locking the position of the shank and the anchor. In some embodiments the deformable insert may comprise a biocompatible polymer.

Referring now to FIGS. 4-8, detailed views of the individual components of the bone compression device 10 are illustrated according to some embodiments. In some embodiments, one or more of the fastener head portion 20, the anchor second end near the shoulder 30, and the locking screw 32 can include a drive portion that accepts a twisting tool such as a screwdriver to threadedly advance or withdraw the component. For example, the fastener head portion 20 includes a recessed drive portion 40, the anchor 26 includes a recessed drive portion 42, and the locking screw 32 includes a recessed drive portion 44. In the embodiments shown, the drive portions are configured as hexalobular recesses with a bore through the center of the drive portions. Other drive configurations may also be used, as the invention is not restricted to hexalobular drives. In particular, raised or recessed drive surfaces, such as would fit a (e.g., hexagonal) wrench may also be used.

In some embodiments three different sizes of recessed drive portions (e.g., hexagonal depressions) are used. The screwdriver that fits the head portion 20 of the fastener 16 may have a ratcheting mechanism such that when the fastener is tightened within the anchor, the anchor is held from turning by one screwdriver and the other screwdriver, with a ratcheting mechanism, is used to turn the fastener into the threaded bore of the anchor. In some cases a screwdriver with a hollow bore and a large hex head on its end may be used. A smaller screwdriver, having a smaller hex head, would then fit through the larger screwdriver and would fit the locking screw 32.

Referring to FIG. 6B, in one embodiment, the anchor drive portion 42 extends about the circumference of the anchor's second end while providing access to the locking screw drive portion 44 through the anchor bore 28. As seen in FIGS. 6A and 6B, in some embodiments, the anchor 26 includes a small, inwardly protruding internal lip 46 at the end of the anchor bore 28 at the second end of the anchor. The lip 46 can be formed integrally with the anchor, and prevents the locking screw 32 from being turned out of the anchor through the second end. Thus, in the event that the locking screw 32 becomes loose after the compression device is installed, the lip 46 can prevent the locking screw 32 from breaking loose into the surrounding body. In some embodiments the lip 46 is rounded and extends around the entire inner circumference of the anchor bore 28. In certain embodiments, however, the lip 46 may be discontinuous, or squared, as desired for a particular implementation. The lip 46 extends inwardly enough to contact the locking screw 32, but not enough to interfere with the drive portion 44 of the locking screw 32.

Figure 9A:
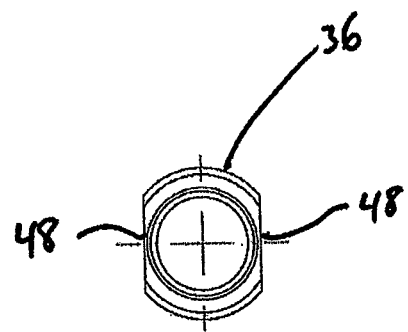
FIG. 9A is a front view of a washer according to an embodiment of the invention.
Figure 9B:
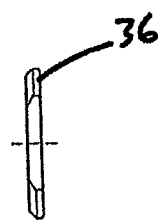
FIG. 9B is a side view of the washer of FIG. 9A.

FIGS. 8A-8C illustrate various views of the washer 38 that may be provided about the fastener head portion 20. FIGS. 9A and 9B illustrate a top and side view of the washer 38 that may be provided about the anchor 26. As can be seen in the Figures, the washers 36, 38, and, for that matter, the fastener head portion 20 and the shoulder 30 of the anchor 26 (FIG. 5B), may have diametrically opposed flat surfaces 48 that can be rotationally positioned so as to reduce the extent to which ends of the device may protrude from the bore holes. In addition, the surfaces of the washers 36, 38 and the fastener head portion 20 and the anchor shoulder 30 that meet can in some cases be chamfered to reduce stress concentrations.

Embodiments of the bone compression device 10 can be used to fix a wide variety of bone fractures, including fractures of the patella. For example, it may be used to secure the calcaneus, the distal femur, the tibia plateau (e.g., using metal plates), and the distal humerus. For ease of understanding of the following description, the device is described as being positioned within the patella with the anchor 26 at the proximal (upper) end of the patella.

Figure 10:
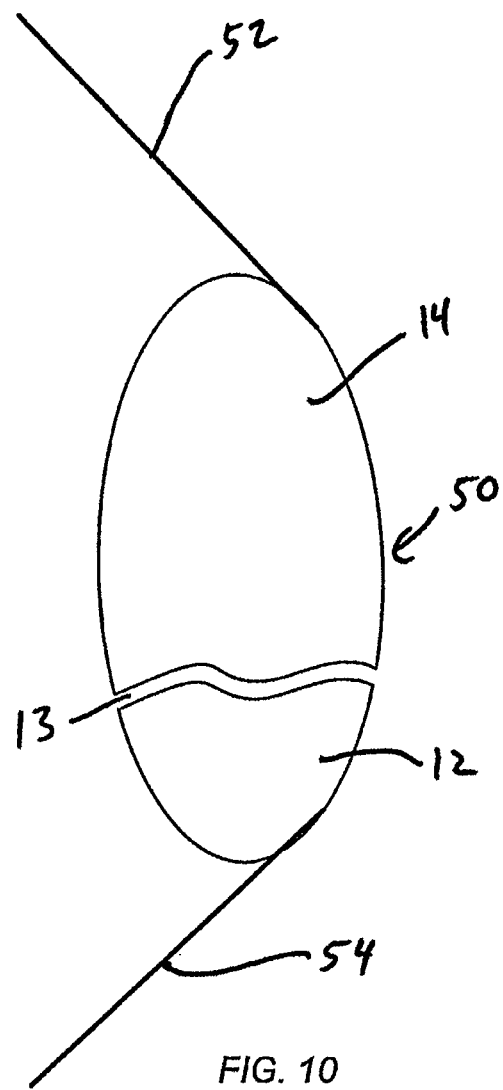
FIG. 10 is a schematic illustration of a fractured patella according to an embodiment of the invention.

Referring to FIG. 10, a schematic illustration of a fractured patella 50 is shown. The patella 50 is normally supported at the knee by the quadriceps tendon 52 from above and the patellar tendon 54 from below, the later being inserted in the tibia. The patella 50 is supported near its middle by contact with the intercondylar groove of the femur. In use, the patella 50 is subjected to substantial bending moments as the knee is bent and weight is placed on the leg. Breakage of the patella under these conditions generally is transverse, that is, side-to-side, with the patella itself tending to open up anteriorally. When used with the patella 50, two spaced bone compression devices 10 can be used for rather common transverse fractures (illustrated in FIG. 10 from the side). In the case of fixing a longitudinal fracture, in some embodiments only one bone compression device may be needed.

According to some embodiments, the bone compression device 10 may be used in one or more methods of fixing two or more bone fragments. For example, a device 10 can be installed through a general knee surgery, in which the patella is laid open through a generally mid-line, longitudinal incision. In a less invasive method, the proximal and distal ends of the patella can be accessed through small incisions. Similar open and subcutaneous procedures may be performed to address fractures of bones other than the patella.

Figure 11:
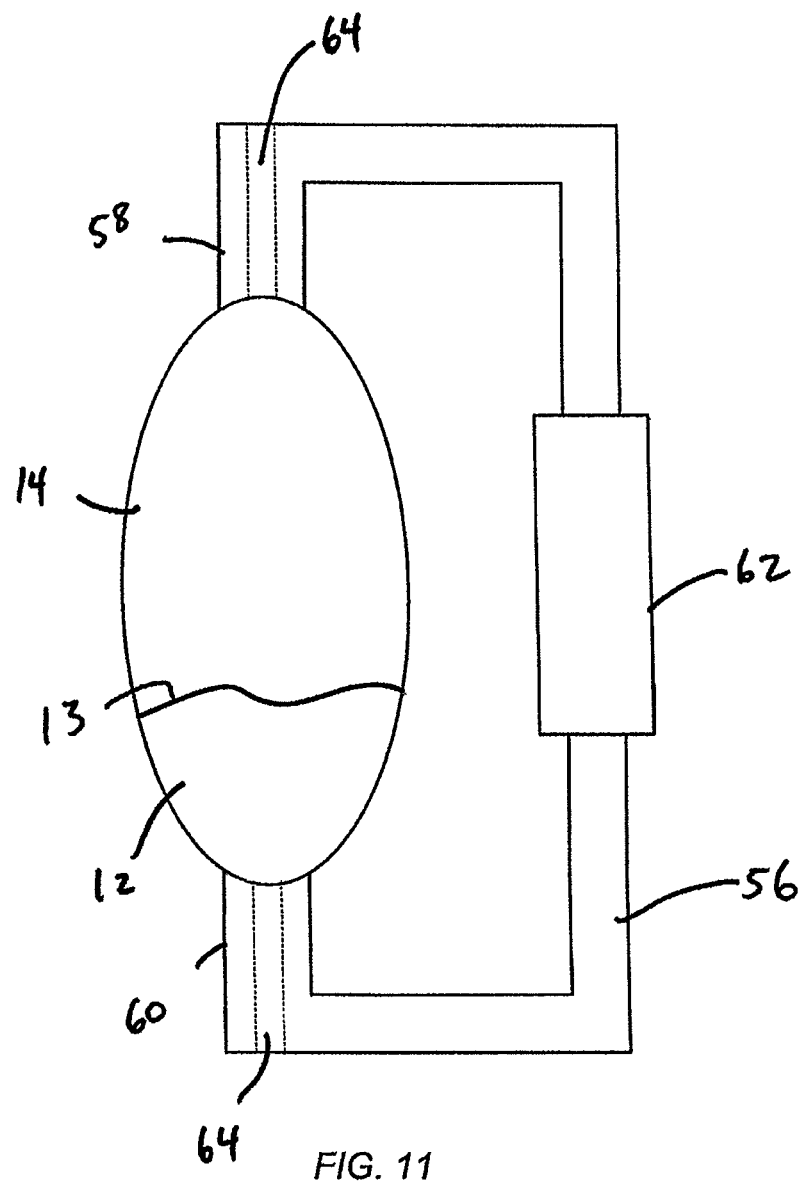
FIG. 11 is a schematic illustration of the fractured patella of FIG. 10 showing use of a clamp to reduce the fracture.

Referring to FIG. 11, in certain embodiments the surgical procedure begins by temporarily fixing the first and second bone fragments 12, 14 with a clamp 56, such as a C-clamp having cannulated jaws. The clamp 56 generally includes first and second jaws 58, 60 for contacting the fractured pieces of bone, an adjustment mechanism 62 for opening and closing the jaws, and a small cannula 64 extending through the jaws. Although perhaps only two bone fragments or fragments result from a simple fracture, if the patella has been injured by a crushing load, sometimes more fragments are formed and must be fit and held together. For this purpose, a C-clamp 56 can be employed to fix the pieces in their correct position while the bores are being formed through the patella.

Figure 12:
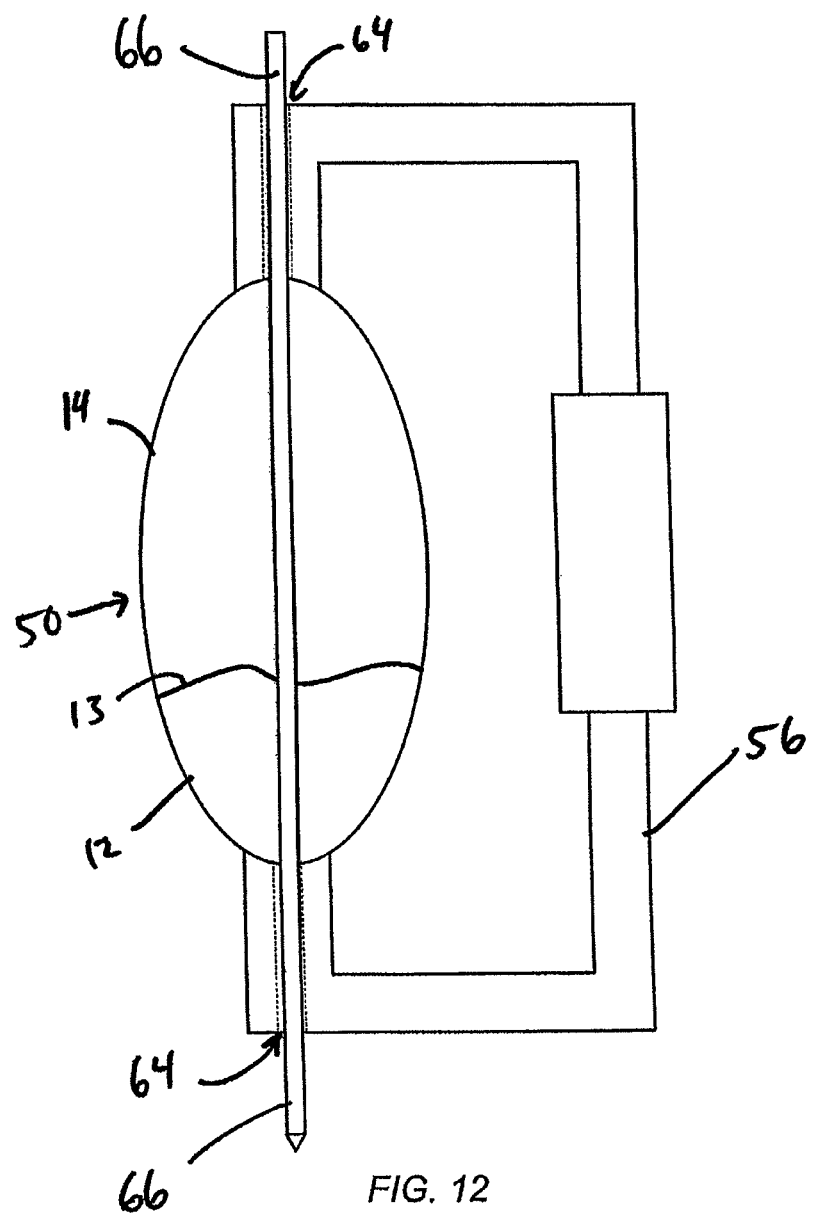
FIG. 12 is a schematic illustration of a Kirschner wire within the fractured patella shown in FIG. 11.

FIG. 12 shows the use of a Kirschner or "K" wire 66 to start a bore hole through the first and second bone fragments 12, 14. According to this embodiment, the patella 50 is prepared by passing the stiff straight wire 66 through the first bone fragment 12, across the fracture line, and through the second bone fragment 14, the wire 66 being placed where the bone compression device 10 will be placed. In some embodiments, insertion of the K wire 66 is guided by the cannulated C-clamp 56 as shown in FIG. 12. For example, in some embodiments the jaws 58, 60 of the clamp 56 may include one or more removable inserts with varying sized bores. The inserts with the smallest bore may guide the K wire 66, the next largest inserts may guide a drill, and larger inserts may guide insertion of the anchor and/or fastener into the bone fragments. The bored inserts may be nested within the jaws in some cases.

Figure 13:
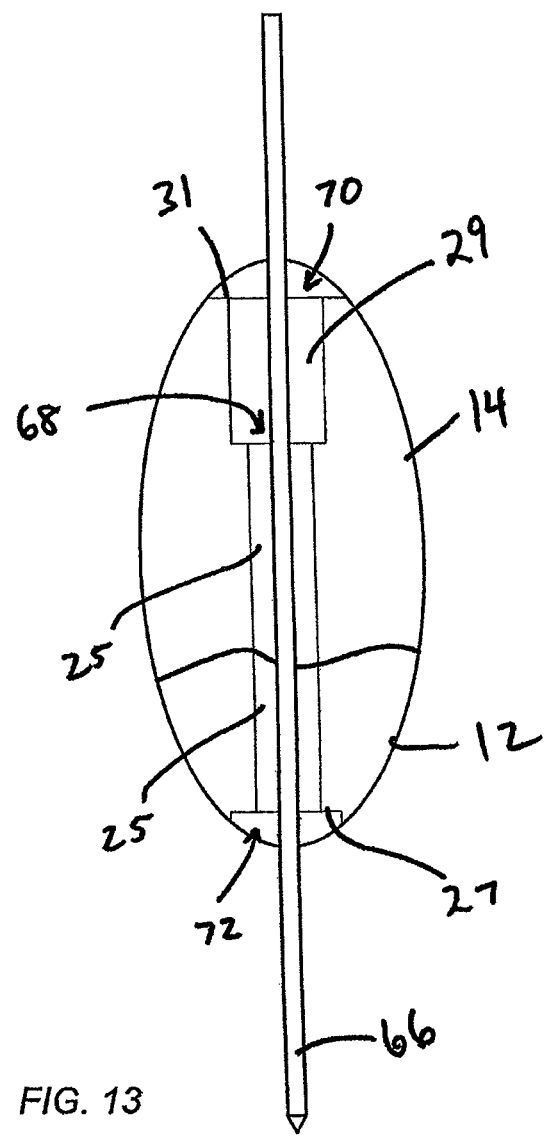
FIG. 13 is a schematic illustration of the patella of FIG. 12, showing bores formed therein.

Turning to FIG. 13, guided by the wire 66, a cannulated bone drill can be used to drill the first bore 25 (see FIG. 1C) through the first bone fragment 12 into the second bone fragment 14 in the proximal direction (that is, upwardly as shown in FIG. 13). The first bore 25 may be very slightly larger than the diameter of the threaded fastener shank portion 22, providing a snug press fit. From the proximal end of the second bone fragment 14, and again guided by the K wire, another, substantially larger second bore 29 is drilled downwardly into the second bone fragment 14 for a predetermined distance, coaxial with the first bore 25.

Preferably, in some embodiments the larger drill for this second bore 29 has an end portion terminating in a squared-off end that provides the second bore 29 with a squared-off floor 68. In some embodiments the larger drill has an enlarged, annular shoulder spaced from its tip to limit the distance to which the drill penetrates into the second bone fragment 14. If desired, the annular shoulder may define a drilling surface configured to produce a short countersunk depression 70 at the rim of the second bore 29 to receive the enlarged shoulder 30 of the anchor 26, or the washer 36 if a washer is used. Similarly, in some embodiments, the drill for the first bore 25 may produce a short countersunk depression 72 at the rim 27 of the first bore 25 to receive the fastener head portion 20 or the washer 38 if one is used. In some embodiments, the washers 36, 38 may be eliminated, particularly when small patients are being treated. If only one washer is used, it preferably is placed on the fastener side. In some cases the washers may include flat opposing edges that can be rotated to limit protrusion of the fastener from the first bore and/or the anchor from the second bore.

Figure 14:
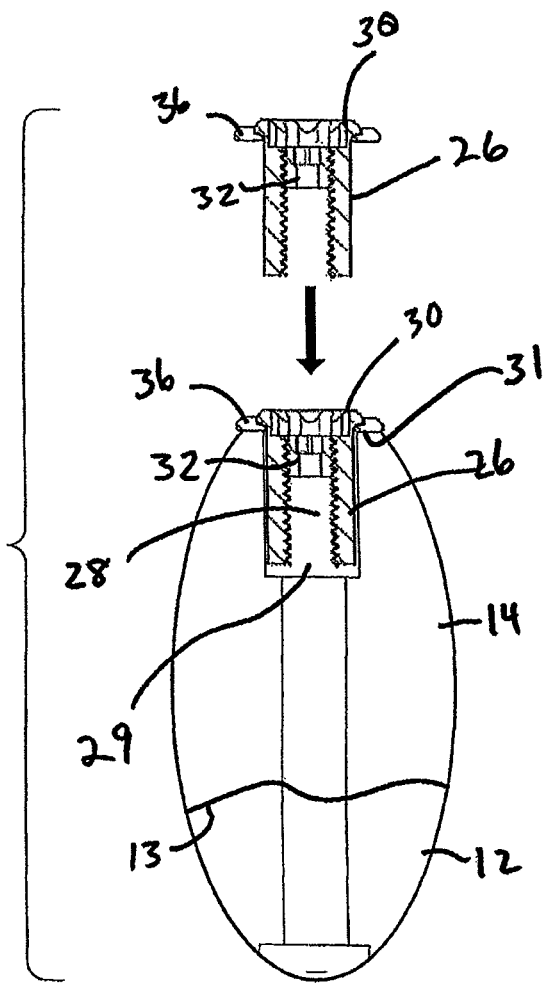
FIG. 14 illustrates the insertion of an anchor into a bore formed in the patella of FIG. 13.
Figure 15:
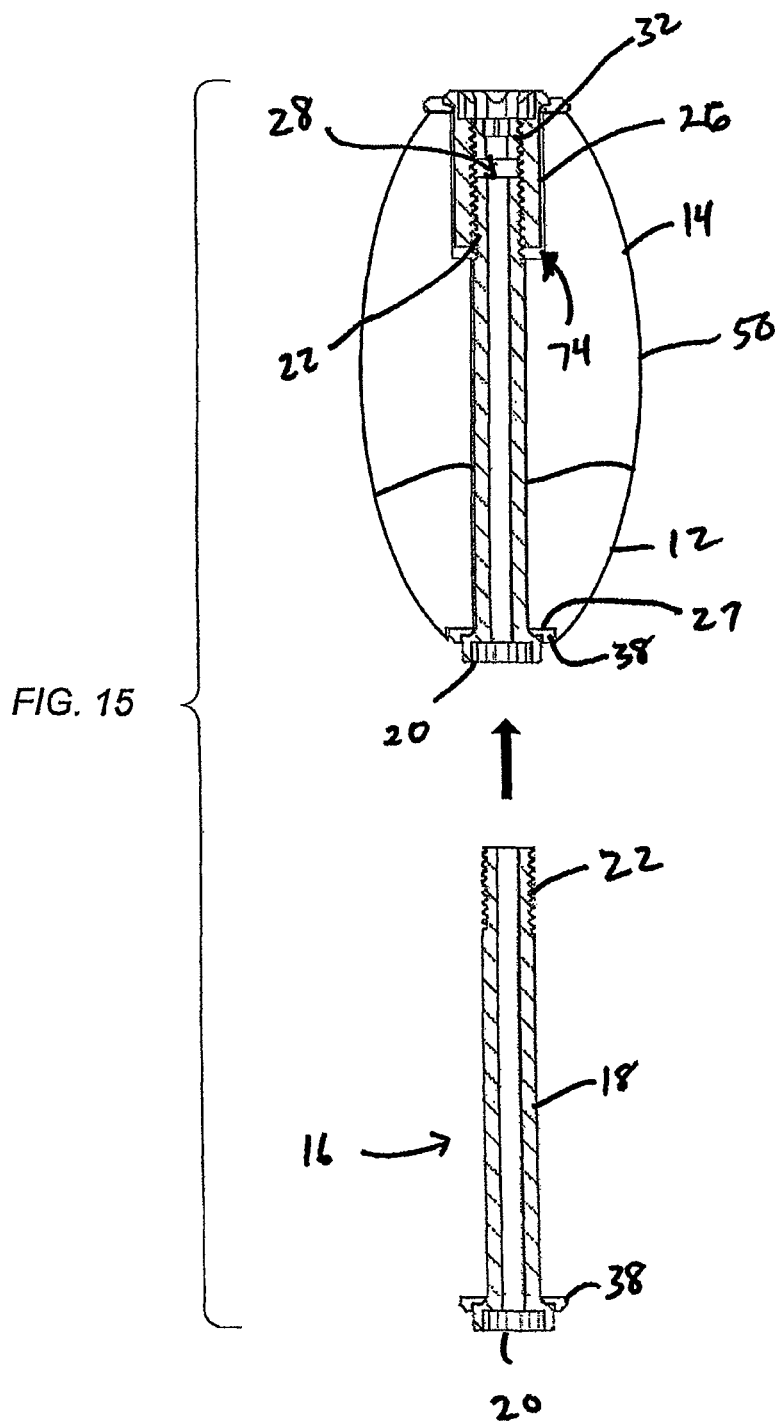
FIG. 15 illustrates the insertion of an elongated fastener.

Referring to FIG. 14, the first end of the anchor 26 is inserted into the second bore 29 such that the anchor shoulder 30 engages the rim 31 of the second bore 29. The anchor contains within it the locking screw 32. As depicted in FIG. 14, the washer 36 provides an intermediate surface through which the shoulder engages the rim. Turning to FIG. 15, the fastener 16 is inserted through the first bore 25 and into the second bore 29. The fastener is advanced so the externally threaded portion 22 of the fastener shank portion 18 threads into the anchor bore 28. The fastener head portion 20 engages the rim 27 of the first bore 25, in this case through the washer 38. As the fastener 16 and the anchor 26 are tightened together, the fastener and anchor compress the first and second bone fragments together to secure the fracture. In some embodiments a surgeon may estimate the amount of needed pressure/compression simply by tightening the fastener and anchor by hand. In other embodiments, a torque measuring or limiting device may be used, although these are not necessarily required.

It should be understood here that the anchor 26, when positioned in the second bore 29, exerts compressive force against the second bone fragment 14 through the contact of the annular shoulder 30 (or the washer 36, if used) with the rim 31 of the bore 29, and not through contact of the confronting, squared-off surfaces 68 of the large bore and the first end of the anchor. These surfaces desirably are separated by a small space 74, perhaps a millimeter in width in some embodiments. In addition, most transverse fractures occur in the lower (distal) one-third of the patella. In such an embodiment, the fastener 16 should be passed through the smaller bone fragment into the larger bone fragment for added strength.

Figure 16:
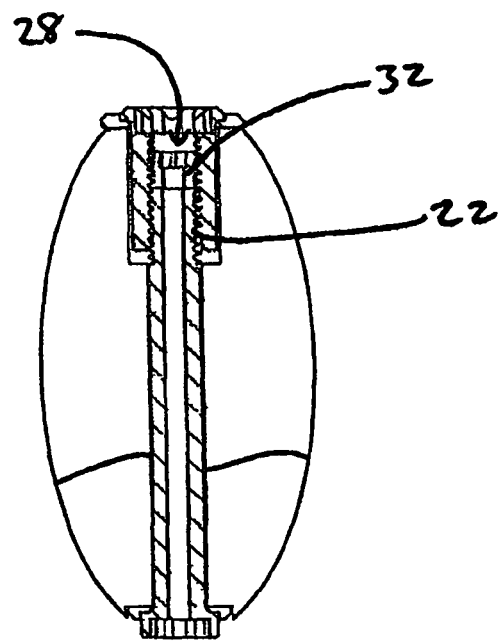
FIG. 16 illustrates the tightening of a locking screw using a twisting tool.

Referring to FIG. 16, the fastener 16 and the anchor 26 are threaded together to provide the desired compression; the locking screw 32 is advanced coaxially through the anchor bore 28 towards the threaded end 22 of the fastener 16. A twisting or driving tool 80, such as a screwdriver, can be used to advance the locking screw 32. The locking screw 32 is turned tightly into the end of the fastener 16 to lock the position of the fastener 16 relative to the anchor bore 28. In some embodiments, turning the locking screw 32 into the fastener end may deform the locking screw and/or the fastener end or the threads of either or both in order to more securely lock the fastener in place to prevent it from backing out of the bore.

As stated before, in some embodiments, the anchor 26 includes an internal lip to prevent the locking screw 32 from backing out of the second bore 29. In such an embodiment, the locking screw 32 may be inserted into the first end of the anchor 26 prior to inserting the anchor into the second bore 29. In other cases, the locking screw 32 may simply be turned into the anchor bore 28 through the second (exterior) end of the anchor 26 when no lip is included.

In some embodiments, the surgical procedure includes a step of selecting a fastener 16 of appropriate length from a plurality of fasteners of different lengths. For example, the anchor 26 may be inserted into the larger second bore, with its shoulder 30 or washer 38 in contact with the rim 31 of the bore and with the locking screw threadingly received and approximately flush with the exterior end of the locking screw 32. A surgeon may then use a measuring rod to determine the distance between the rim 27 of the smaller bore and the confronting end of the locking screw. An appropriate fastener 16 is chosen having a length such that the end of the threaded shank portion 22 will be spaced slightly from the confronting end of the locking screw when the fastener 16 is threaded into the anchor and the desired compression of the fracture edges of the bone has been achieved. The locking screw 32 is then threaded further into the anchor bore 28 into locking engagement with the end of the fastener 16, to prevent the fastener from backing out of the bore 25.

Most fractures of the patella are transverse to the long direction of the leg, due at least in part to the forces on the patella exerted by the quadriceps and patellar tendons and the geometry of the patella/femoral condyles. In some embodiments of the invention, a surgical procedure may include providing a second (or even a third) bone compression device 10 which is then inserted into the first and second bone fragments across the fracture and spaced a distance away from the first bone compression device.

Figure 17:
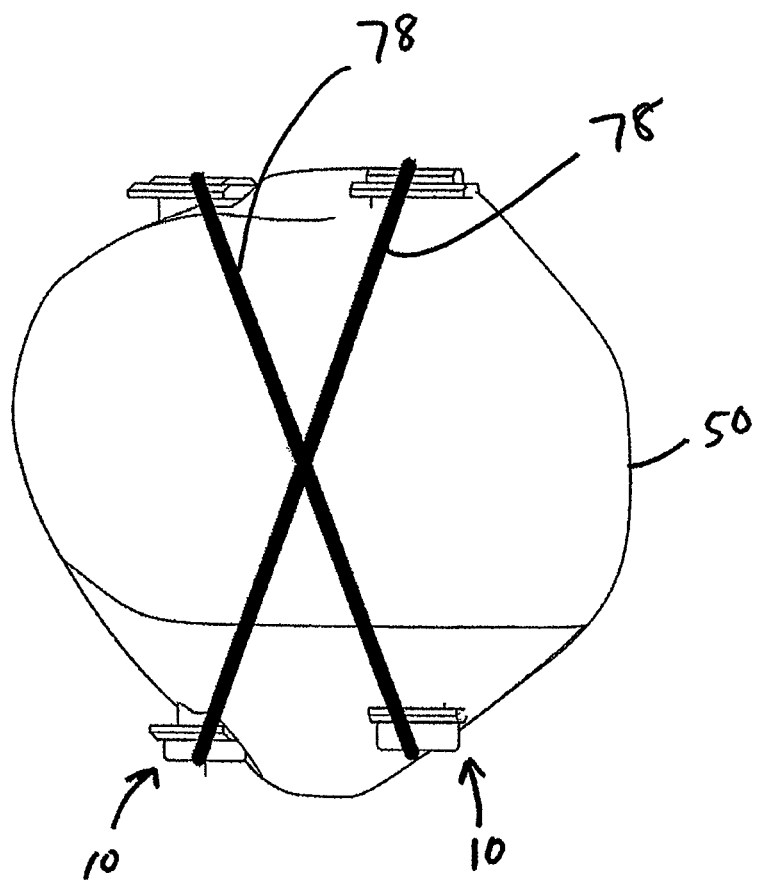
FIG. 17 is a schematic illustration of a fractured patella fixed by tension bands according to an embodiment of the invention.

After placing and tightening one or more bone compression devices, the bone fragments may not yet be completely stabilized. For example, movement between some of the patella fragments may yet occur. Referring to FIG. 17, to reduce the tendency for movement, various surgical wires 78 may be passed through the open interiors of the compression devices, and may be appropriately strung together, as in a figure eight configuration, to further immobilize the patella. Such a method may include using circlage wires to further stabilize the fracture. In some embodiments the wires are fed into place using tools, so that the whole operation can be performed through small incisions.

In addition to a bone compression device and method of installing and using bone compression devices, in some embodiments the invention provides one or more kits for compressing together first and second bone fragments. One exemplary kit includes a plurality of fasteners 16, such as those previously described, having different lengths, along with at least one anchor with a lock (e.g., externally threaded locking screw) as previously described. In some cases, a kit may include a number of anchors and locking screws, multiple driving tools, Kirschner wires, tension bands, and/or a cannulated clamp. In some cases a kit may further include a deformable insert, receivable within the anchor bore between the second end of the fastener shank and the locking screw to deform and lock the position of the fastener shank when the fastener shank and the locking screw are tightened against each other.

Thus, embodiments of the BONE COMPRESSION DEVICE AND METHODS are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A method of compressing together first and second bone fragments using at least one bone compression device, comprising:

providing a first bone compression device having a fastener including a shank portion with an externally threaded portion and first and second ends and an enlarged head portion coupled to the first end and a bore extending through the head and shank portions, an anchor having first and second ends with an internally threaded bore and an enlarged shoulder at the second end, and a lock;

forming a first bore through the first bone fragment and at east partially through the second bone fragment;

forming a second bore through the second bone fragment connecting to and coaxial with the first bore, the second bore having a greater diameter than the first bore;

inserting the first end of the anchor into the second bore such that the anchor shoulder engages a rim of the second bore and such that the first end of the anchor is positioned one millimeter from an interface of the second bore with the first bore;

inserting the fastener through the first bore and into the second bore and advancing the externally threaded portion of the fastener shank portion into the first end of the anchor so that the fastener head portion engages a rim of the first bore and the fastener and anchor compress the first and second bone fragments together; and advancing the lock through the anchor towards the fastener and engaging the second end of the fastener shank portion to lock the relative positions of the fastener and the anchor.

2. The method of claim 1, wherein the lock comprises an externally threaded locking screw having a bore therethrough, and wherein advancing the lock comprises advancing the locking screw coaxially through the anchor towards the fastener and engaging the second end of the fastener shank portion to lock the relative positions of the fastener and the anchor.

3. The method of claim 2, further comprising inserting the locking screw into the first end of the anchor prior to inserting the anchor into the second bore.

4. The method of claim 3, further comprising preventing removal of the locking screw through the second end of the anchor.

5. The method of claim 1, further comprising forming a countersunk depression in the first bone fragment about the rim of the first bore, wherein inserting the fastener through the first bore further comprises positioning the fastener head portion within the countersunk depression about the rim of the first bore.

6. The method of claim 1, further comprising forming a countersunk depression in the second bone about the rim of the second bore, wherein inserting the anchor into the second bore further comprises positioning the anchor shoulder within the countersunk depression about the rim of the second bore.

7. The method of claim 1, further comprising squaring off the second bore at the interface of the second bore with the first bore.

8. The method of claim 1, further comprising providing a first washer about a circumference of the anchor and a second washer about the fastener, wherein the anchor shoulder engages the rim of the second bore through contact with the first washer and wherein the fastener head portion engages the rim of the first bore through contact with the second washer.

9. The method of claim 8, further comprising rotating at least one of the first and second washers to limit protrusion of the fastener from the first bore and/or the anchor from the second bore.

10. The method of claim 1, further comprising selecting the fastener of the first bone compression device from a plurality of fasteners of different lengths, such that the threaded portion of the fastener shank portion will be substantially received within the anchor when the fastener and the anchor compress the first and second bone fragments to a desired degree.

11. The method of claim 1, further comprising inserting a Kirschner wire through the first and second bone fragments as a guide for forming the first and second bores.

12. The method of claim 11, further comprising temporarily fixing the first and second bone fragments with a cannulated clamp, and inserting the Kirschner wire into the first and second bone fragments through a clamp cannula.

13. The method of claim 1, wherein the first and second bone fragments are separated by a fracture.

14. The method of claim 13, wherein the first and second bone fragments form at least a portion of a patella.

15. The method of claim 14, wherein the method is completed as part of a knee resection procedure.

16. The method of claim 13, wherein the first and second bone fragments form at least a portion of at least one of a femur, a tibia, a calcaneus, and a humerus.

17. The method of claim 13, wherein the method is completed as part of a subcutaneous procedure.

18. The method of claim 13, further comprising providing a second bone compression device inserted into third and fourth bores across the fracture a distance away from the first bone compression device.

19. The method of claim 18, further comprising using cerclage wires to further stabilize the fracture.

* * * * *